United States Patent [19]

Daughenbaugh

[11] 4,258,200
[45] Mar. 24, 1981

[54] PRODUCTION OF CARBOXYLIC ACID AMIDES AND CARBAMATES USING COBALT CATALYSTS

[75] Inventor: Randall J. Daughenbaugh, Barto, Pa.

[73] Assignee: Air Products and Chemicals, Inc., Allentown, Pa.

[21] Appl. No.: 129,453

[22] Filed: Mar. 11, 1980

[51] Int. Cl.³ .......................................... C07C 102/06
[52] U.S. Cl. ...................................... 560/24; 260/404; 560/32; 560/132; 560/153; 560/163; 564/135; 564/137
[58] Field of Search ............... 260/561 R, 562 R, 404; 560/24, 32, 132, 157, 163

[56] References Cited

U.S. PATENT DOCUMENTS

| Re. 29,369 | 8/1977 | Fujimoto | 560/32 |
| 2,667,511 | 1/1954 | Downing | 260/561 |
| 3,197,450 | 7/1965 | Tsou | 260/913 |
| 3,342,862 | 9/1967 | Board et al. | 260/561 |
| 3,407,231 | 10/1968 | Nozaki | 260/561 |
| 3,538,159 | 11/1970 | Duffy | 260/561 |
| 3,763,217 | 10/1973 | Brill | 560/24 |
| 3,763,234 | 10/1973 | Brill | 260/562 R |
| 3,816,483 | 6/1974 | Werdehausen et al. | 260/561 R |
| 4,097,676 | 6/1978 | Romano et al. | 560/132 |
| 4,100,351 | 7/1978 | Romano et al. | 560/24 |

*Primary Examiner*—Arthur P. Demers
*Attorney, Agent, or Firm*—E. Eugene Innis; Russell L. Brewer

[57] ABSTRACT

Carboxylic acid amides are produced by the catalytic reaction of an ester and an amine is shown. Organo cobalt salts are used as the catalyst. The process is particularly useful for producing dimethylacetamide by the reaction of methyl acetate and dimethylamine.

15 Claims, 1 Drawing Figure

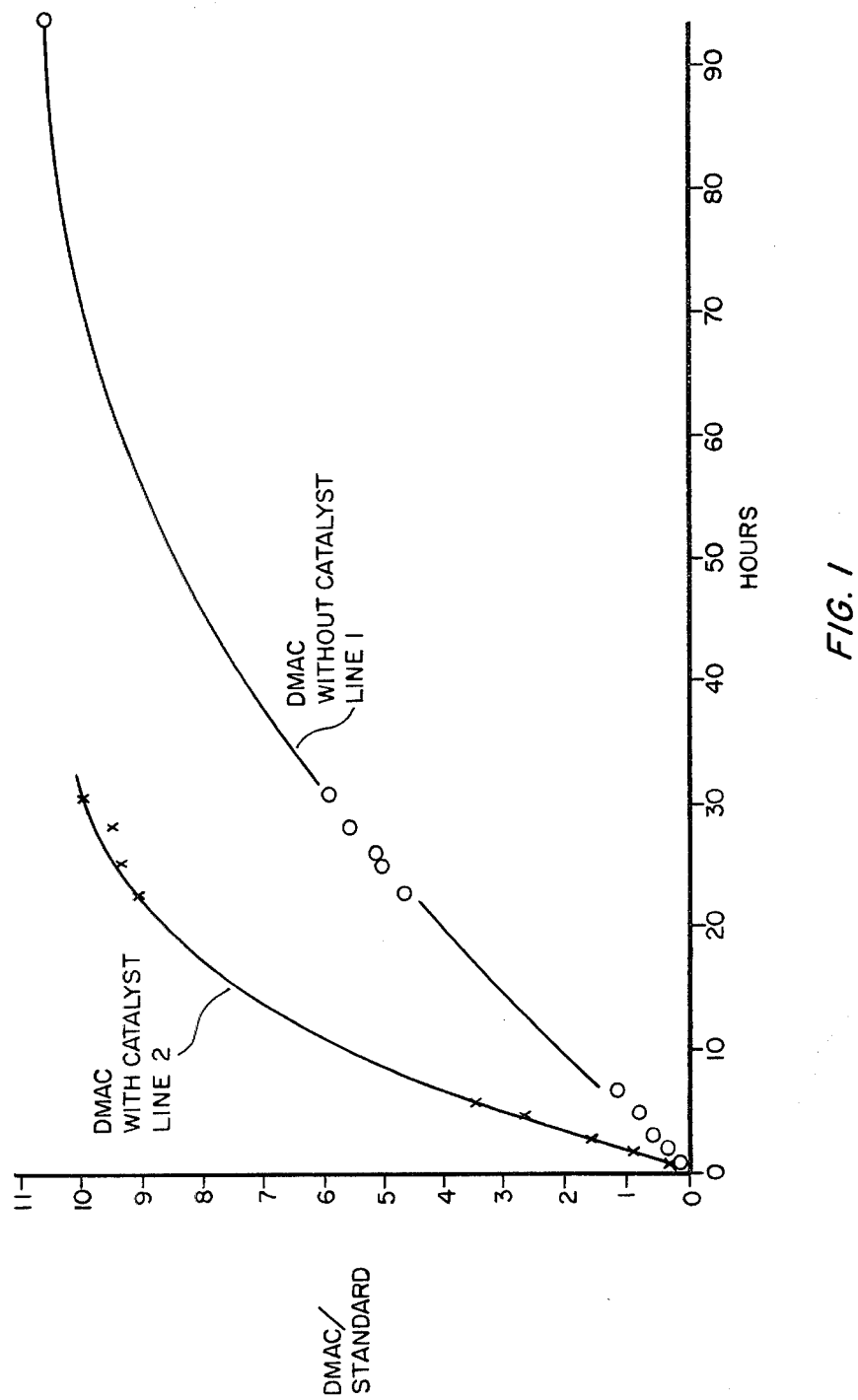

PRODUCTION OF CARBOXYLIC ACID AMIDES AND CARBAMATES USING COBALT CATALYSTS

BACKGROUND OF THE INVENTION

1. Field of the Invention

This invention relates to a process for producing carboxylic acid amides by the reaction of an ester and an amine and carbamate by the reaction of a diester of carbonic acid and amine.

2. Description of the Prior Art

U.S. Pat. No. 3,342,862 relates to a process for producing dimethylacetamide by the reaction of dimethylamine and an alkyl ester, namely methyl acetate. The reaction involves passing excess gaseous dimethylamine and an aqueous solution of an alkyl ester through a packed column reactor to produce a dimethylacetamide and one mole of alcohol by-product.

U.S. Pat. No. 3,538,159 discloses a process of producing di-N-methylamides by catalytically reacting dimethylamine with an alkyl ester in the presence of a strongly alkaline compound of an alkali metal. Examples are sodium alkoxides, sodium ethylene glycollate, etc. The reaction is carried out at a temperature from about 15° to 130° C. The reaction pressure commonly used is from 1 to 50 atmospheres.

U.S. Pat. No. 3,197,450 discloses a process producing dimethylacetamide and polyvinyl alcohol by reacting a solution of a polyvinyl acetate and an alcohol solvent containing dialkyl amine. Temperature from 0° to 75° C. and pressures of 25-50 psig generally are used to carry out the reaction.

U.S. Pat. No. 3,407,231 dislcoses a process for producing dimethylacetamide by the carbonylation of trimethylamine in the presence of dicobalt octacarbonyl, the octacarbonyl used in a catalytic amount. Reaction temperatures generally are from about 175° to 275° C. with pressures generally from 1000-6000 psig.

U.S. Pat. No. 2,667,511 discloses a process for producing alkyl-substituted acylamides by reacting an acyl compound with dimethylamine.

SUMMARY OF THE INVENTION

This invention relates to an improvement in a process producing a carboxylic acid amide or a substituted carbamate by the reaction of (1) a carboxylic acid ester of a fatty acid of one to twelve carbon atoms and an alkanol of one to twelve carbon atome or (2) a $C_{1-12}$ diester of carbonic acid with an amine selected from the group consisting of a hydrocarbon primary and secondary amine having from one to twelve carbon atoms including aromatic amines i.e. aniline etc. The improvement resides in the use of an organo-cobalt composition where the cobalt is in its +2 valence state. The cobalt salt generally is employed in a proportion of about 0.001 to 0.15 moles per mole of ester feed.

Advantages of this process are several. The organo-cobalt materials are extremely effective in catalyzing the reaction of the ester and amine to produce carboxylic acid amines and thus the reaction rate is substantially increased as compared to a noncatalytic reaction.

The catalyst permits the reaction at low pressures thus permitting the process to be carried out with lower energy requirements and low pressure equipment.

THE DRAWINGS

The FIGURE is a plot of the ratio of dimethylacetamide vis-a-vis an internal standard versus time under conditions of (a) no catalyst, and (b) 1.5 mol % cobalt II catalyst.

DESCRIPTION OF PREFERRED EMBODIMENTS

The reaction of a carboxylic acid ester plus an amine to form a carboxylic acid amide and an alcohol is known. Also the reaction of a carbonic acid ester and amine to form a carbamates is known. The carboxylic acid esters that are used for such reaction generally are those derived from fatty acids having from one to twelve carbon atoms and alkanols having from one to twelve carbon atoms with particular emphasis on the $C_1$ and $C_2$ fatty acids and alkanols. Examples of specific compositions suited for the process include: methyl formate, ethyl formate, butyl formate, methyl acetate, methyl propionate and the like. Carbonate esters are widely accepted to undergo reactions in a like manner to that of the above carboxylic acid esters and therefore $C_{1-12}$ diesters of carbonic acid with emphasis on the $C_{1-2}$ alkyl esters are included. Examples include dimethyl and diethyl carbonate.

The amines suited for reaction with the carboxylic acid esters are of the primary and secondary types. These amines can have from one to twelve carbon atoms in the structure. Examples of suitable amines are: methylamine, dimethylamine, ethylamine, diethylamine, ethylmethylamine, dibutylamine, cyclohexylamine, dicyclohexylamine, and aromatic amines, aniline, toluene diamine benzylamine, methylene dianiline.

Of the carboxylic acid esters and amines listed above, methylacetate and dimethylamine are preferred in that the end product, dimethylacetamide, has substantial commercial appeal. Carbanilates, like that derived from aniline and diethylcarbonate are of interest because they have been shown to be intermediates in the formation of isocyanates.

The carboxylic acid esters and the amines are reacted together in stoichiometric amounts to produce the amide or carbamate; however, it is often advantageous to use an excess of amine. The reaction temperature for the process is generally from about 30° to 300° C. with pressures of 0 to 600 psig. Preferably temperatures from 50° to 200° C. and pressures from 30 to 300 psig are used in the process. Generally lower temperatures e.g., 50°-100° C. can be used for preparing the amides whereas higher temperatures 140°-180° are used to prepare the carbamates.

It has been found that organo-cobalt salts where the cobalt is in its +2 valence state are effective for catalyzing the reaction between the ester and amine to form the amide. To provide for homogeneous catalysis, the organo-cobalt salts should be soluble or dispersible in the reaction mixture. Solubility of the catalyst in the reactants or at least in a carrier solvent having affinity for the reactants is necessary for the homogeneous catalytic reaction. Preferred cobalt salts are cobalt salts of monocarboxylic acids having from one to twelve carbon atoms, preferably alicyclic saturated hydrocarbons. Examples include cobalt acetate, cobalt propionate, cobalt napthenate, and the like.

The organo cobalt salt is incorporated into the reaction medium in an amount to provide from about 0.001 to 0.15 moles cobalt metal per mole of carboxylic acid ester or diester of carbonic acid. In typical runs, the level of cobalt metal is from about 1 to 5 mole % of the carboxylic acid ester or diester of carbonic acid.

As in conventional processes, an inert carrier solvent can be used to promote heat transfer and provide a carrier for the catalyst and the reactants. In the event a carrier solvent is used, the catalyst need not have the degree of solubility in the reactants as set forth. Solubility in the carrier is sufficient for the reaction. Examples of inert carriers include water, methanol, ether, etc.

The following examples are provided to illustrate preferred embodiments of the invention and are not intended to restrict the scope thereof.

EXAMPLE 1

Dimethylacetamide was prepared by first charging 70 ml of a 20% methanol-methylacetate azeotrope to a 300 ml stirred autoclave (0.735 moles methylacetate). Then 73 ml of dimethylamine (1.1 moles dimethylamine), which is sufficient to provide 50% excess of the stoichiometric quantity of a dimethylamine based on methylacetate, was charged to the autoclave. A catalyst consisting of 0.011 moles cobalt (II) acetate tetrahydrate was added to the mixture. The reaction was carried out at a temperature of 155°-160° F. with the initial pressure being approximately 55 psig. The concentration of dimethylacetamide was determined periodically by gc analysis using dimethyl formamide as an internal standard. (The ratio of dimethylacetamide to the standard is indicative of concentration.)

The rate of dimethylacetamide formation versus time in the presence of catalyst was plotted in the FIGURE, line 2. These results show that when the same procedure was carried out under the same identical conditions, but in the absence of any catalyst, the reaction rate was substantially slower. Line 1 represents the rate of dimethylacetamide formation in the absence of catalyst.

The procedure used above for cobalt (II) acetate tetrahydrate was repeated except that 0.011 moles of cobaltic acetylacetonate were substituted for the cobalt (II) acetate tetrahydrate. The cobalt III salt was ineffective as a catalyst under these conditions.

EXAMPLE 2

Twenty ml of aniline and 20 ml of dimethyl carbonate were charged to a 128 ml Parr pressure vessel. After heating at 100° C. for 95 hours, gc analysis showed the reaction mixture to be 5.2% N-methylaniline, 0.02% methyl carbanilate and a trace amount of N-methyl-methylcarbanilate, the remainder being starting material. This mixture was then heated at 115° C. for an additional 72 hours. Analysis showed 8.7% N-methylaniline, 0.04% methyl carbanilate and a trace amount of N-methyl-methyl carbanilate for the 167 hour reaction.

The above procedure was repeated except that 232 mg of cobalt acetate tetrahydrate was added to the reaction mixture. After 145 hours at 100° C. Analysis showed 2.7% N-methylaniline, 1.1% methyl carbanilate and a trace amount of N-methyl-methyl carbanilate.

The above experiment with 232 mg of cobalt (II) acetate tetrahydrate was repeated but at higher temperatures. After 15 hours at 164° C. analysis showed 8.4% N-methylaniline, 6.2% methyl carbanilate, and a trace amount of N-methyl-methyl carbanilate.

These examples show the utility of the cobalt (II) acetate tetrahydrate catalyst for increasing the selectivity to the desired methyl carbanilate. The results also shown conversions increase at higher temperatures.

EXAMPLE 3

Twenty ml of aniline, 20 ml of diethylcarbonate, and 223 mg cobalt (II) acetate tetrahydrate were charged to a 128 ml Parr pressure vessel, and heated to 160° C. Analysis showed the percentages of N-ethyl aniline, and the desired ethyl carbanilate indicated in the table.

| Reaction time, hours | Reaction Products N-ethylaniline | Ethylcarbanilate |
|---|---|---|
| 19 | 0.67 | 1.21 |
| 24 | 7.26 | 16.28 |
| 45 | 15.84 | 18.81* |

*This represents a saturated solution. Most of the product had precipitated from solution.

This example shows the utility of cobalt (II) acetate in the formation of ethyl carbanilate. When comparing this example to Example 2 it is believed the increased yield to product was not a function of temperature but rather a function of the catalytic activity of the catalyst.

What is claimed is:

1. In a process for producing a (1) carboxylic acid amide by reacting a carboxylic acid ester of a fatty acid of 1 to 12 carbon atoms and an alcohol of 1 to 12 carbon atoms with an amine selected from the group consisting of primary and secondary amines of 1 to 12 carbon atoms or (2) a carbamate by reacting a $C_{1-12}$ diester of carbonic acid with an amine selected from the group consisting of primary and secondry amines of 1–12 carbon atoms, the improvement for enhancing the reaction rate which comprises including a catalytic amount of an organo cobalt catalyst where the cobalt is in its +2 valence state.

2. The process of claim 1 wherein said reaction is carried out at a temperature of from 30° to 300° C. and a pressure of from 0 to 600 psig.

3. The process of claim 2 wherein an amide is produced and said carboxylic acid ester is an alkyl acetate.

4. The process of claim 3 wherein said amine is a dialkyl amine.

5. The process of claim 4 wherein said cobalt salt is a cobalt salt of a monocarboxylic acid having from 1–12 carbon atoms.

6. The process of claim 5 wherein said cobalt salt of a monocarboxylic acid is present in a proportion to provide from about 0.001 to 0.15 moles cobalt per mole of carboxylic acid ester in the reaction.

7. The process of claim 6 wherein said carboxylic acid ester is methyl acetate and said dialkyl amine is dimethylamine.

8. The process of claim 7 wherein said cobalt catalyst is cobalt acetate and the reaction temperature is from 50°–100° C.

9. The process of claim 8 wherein said cobalt acetate is in the tetrahydrate form.

10. The process of claim 2 wherein a carbamate is produced and the diester of carbonic acid is a dialkyl ester of carbonic acid.

11. The process of claim 10 wherein said amine is an aromatic amine.

12. The process of claim 11 wherein said aromatic amine is selected from the group consisting of toluene diamine, aniline, benzylamine or methylene dianiline.

13. The process of claim 10 wherein said cobalt salt is a cobalt salt of a monocarboxylic acid.

14. The process of claim 13 wherein said cobalt salt is included in a proportion of from 0.001–0.15 moles cobalt per mole of diester of carbonic acid feed.

15. The process of claim 14 wherein said cobalt salt is cobalt acetate and the reaction temperature is from about 140°–180° C.

* * * * *